United States Patent
Eggli et al.

(10) Patent No.: US 10,729,317 B2
(45) Date of Patent: Aug. 4, 2020

(54) INTUBATION INSTRUMENT

(71) Applicant: Karl Storz SE & Co. KG, Tuttlingen (DE)

(72) Inventors: Armin Eggli, Uhwiesen (CH); Cyrill Künzle, Winterthur (CH); Dieter Hüls, Stockach (DE); Ulrich Merz, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 393 days.

(21) Appl. No.: 15/606,958

(22) Filed: May 26, 2017

(65) Prior Publication Data

US 2018/0338675 A1   Nov. 29, 2018

(51) Int. Cl.
| | | |
|---|---|---|
| *A61B 1/06* | (2006.01) | |
| *A61B 1/267* | (2006.01) | |
| *A61B 1/005* | (2006.01) | |
| *A61B 1/00* | (2006.01) | |
| *A61B 1/07* | (2006.01) | |

(52) U.S. Cl.
CPC .......... *A61B 1/267* (2013.01); *A61B 1/00039* (2013.01); *A61B 1/00048* (2013.01); *A61B 1/0052* (2013.01); *A61B 1/00052* (2013.01); *A61B 1/00055* (2013.01); *A61B 1/00066* (2013.01); *A61B 1/07* (2013.01)

(58) Field of Classification Search
CPC ..... A61B 1/267; A61B 1/005; A61B 1/00163; A61B 1/00131; A61B 1/00045; A61B 1/00; A61B 1/00052; A61B 1/00064; A61B 1/0052; A61B 1/07; A61B 1/06; A61B 1/0683; A61B 1/0661; A61B 1/0669; A61B 1/0676; A61B 1/0684; A61B 1/0692; A61B 1/042; B25G 1/00; B25G 1/10; F21V 23/0414; F21Y 2113/10; F21Y 2113/13; F21Y 2113/17; H01H 2009/164; H01H 3/12; H01H 9/161
USPC .................. 600/101–183, 185–249; 81/489; 200/313, 314; 362/119; 340/815.56
See application file for complete search history.

(56) References Cited

U.S. PATENT DOCUMENTS

| | | | |
|---|---|---|---|
| 5,001,556 A * | 3/1991 | Nakamura | A61B 1/00009 348/70 |
| 6,319,195 B1 | 11/2001 | Nakaichi et al. | |
| 7,608,039 B1 * | 10/2009 | Todd | A61B 1/00039 200/310 |

(Continued)

*Primary Examiner* — Kevin T Truong
(74) *Attorney, Agent, or Firm* — Whitmyer IP Group LLC (57) ABSTRACT

An intubation instrument includes a proximal end and a distal end, a handle positioned at the proximal end, a control interface disposed on or proximate to the handle, the control interface being configured to receive user input and to control a function of the instrument based on said user input, the control interface having a light source disposed within the control interface to illuminate at least a portion of the control interface, the light source alternately emitting light in different colors, each color indicating a different state of the function of the instrument. The instrument includes an imaging system for generating image data, and a monitor for displaying the image data and a graphical interface. A section of the graphical interface includes information about the state of the instrument and is displayed in a color corresponding to the color of light emitted by the light source of the control interface.

23 Claims, 5 Drawing Sheets

(56) References Cited

U.S. PATENT DOCUMENTS

| | | | |
|---|---|---|---|
| 7,946,981 B1* | 5/2011 | Cubb | A61B 1/00052 600/120 |
| 8,746,239 B2* | 6/2014 | Yoshida | A61B 90/30 128/200.26 |
| 9,095,298 B2* | 8/2015 | Ashcraft | A61B 1/267 600/186 |
| 10,028,360 B1* | 7/2018 | Chen | H05B 37/0281 |
| 2002/0022769 A1* | 2/2002 | Smith | A61B 1/00052 600/188 |
| 2002/0087050 A1* | 7/2002 | Rudischhauser | A61B 1/267 600/199 |
| 2004/0122292 A1* | 6/2004 | Dey | A61B 1/0676 600/190 |
| 2008/0218998 A1* | 9/2008 | Quest | G01M 3/38 362/230 |
| 2008/0249355 A1* | 10/2008 | Birnkrant | A61B 1/00105 600/112 |
| 2008/0272714 A1* | 11/2008 | Noble | F21L 4/027 315/292 |
| 2008/0312507 A1* | 12/2008 | Kim | A61B 1/00052 600/188 |
| 2008/0312649 A1* | 12/2008 | Guerra | A61B 18/1445 606/41 |
| 2009/0318769 A1* | 12/2009 | Tenger | A61B 1/043 600/199 |
| 2010/0095969 A1* | 4/2010 | Schwartz | A61M 25/0136 128/207.14 |
| 2011/0028790 A1* | 2/2011 | Farr | A61B 1/00052 348/77 |
| 2012/0169481 A1 | 7/2012 | Tydlaska et al. | |
| 2012/0178997 A1* | 7/2012 | Tydlaska | A61B 1/00052 600/186 |
| 2012/0330104 A1* | 12/2012 | Tenger | A61B 1/0684 600/191 |
| 2013/0190568 A1* | 7/2013 | Hakanen | A61B 1/267 600/186 |
| 2014/0107416 A1* | 4/2014 | Birnkrant | A61B 1/00016 600/110 |
| 2014/0309495 A1* | 10/2014 | Kirma | G02B 23/243 600/109 |
| 2016/0051781 A1* | 2/2016 | Isaacs | A61M 16/0488 600/188 |
| 2016/0174819 A1* | 6/2016 | Ouyang | A61B 1/00103 600/105 |
| 2016/0256047 A1* | 9/2016 | Newcomb | A61B 1/267 600/186 |
| 2016/0317009 A1 | 11/2016 | Brambrink et al. | |

* cited by examiner

INTUBATION INSTRUMENT

TECHNICAL FIELD

The present disclosure generally relates to the field of intubation instruments, including laryngoscopes and endoscopes that are configured to be used in the field of intubation, such as intubation video endoscopes. More particularly, the present disclosure relates to the control interface of intubation instruments.

BACKGROUND

During medical emergencies, the need to aid a patient's breathing often becomes necessary. Tracheal intubation with an oral airway (oral tracheal airway) for ventilation of a patient's lungs is an operation of critical importance. An incorrect intubation, in which the airway is inserted into the esophagus instead of the trachea, could result in anoxia, brain damage, and death as air fails to reach the lungs. The patient's lungs are completely cut off from oxygen if the airway is wrongly inserted.

In addition to correct intubation, instruments are required by which means for ventilating the patient may be inserted in the trachea as quickly as possible. This requirement is particularly necessary for emergency intubations, which occur for example after accidents in which the trachea and, as a consequence, the respiration of the patient is strongly restricted or entirely blocked. Emergency situations of that kind occur in connection with work accidents, road accidents and particularly motor cycle accidents. For such an emergency intubation, an instrument needs to be provided which is preferably operable in a simple and reliable fashion.

Conventional laryngoscopes include a handle that carries batteries or another similar power source. Attached to the handle is a blade portion that may include a light source. The medical professional will position the blade portion of the laryngoscope in the oropharynx of a patient in an attempt to gain access to the patient's airway. During this step, the light source in the blade portion will illuminate and give the medical professional an improved view of the patient's airway. However, with conventional laryngoscopes and intubation instruments, visualization of the larynx is often inadequate or even impossible as a patient's anatomical conditions or characteristics make laryngoscopy difficult.

Some intubation endoscopes have been developed to provide increased visualization of an airway passage during the procedure. In some embodiments, the intubation endoscope comprises a flexible tube having an image sensor mounted at its distal end. The intubation endoscope is used in conjunction with a conventional laryngoscope such that an airway passage is visualized during the intubation process by utilizing the laryngoscope to open the airway passage and to simultaneously insert in the airway the intubation endoscope to provide imaging of the region of interest. Such an intubation endoscope is known from U.S. Pat. No. 6,319,195.

However, conventional intubation instruments still fail to provide simple and reliable operation, especially with respect to visualization during an intubation procedure. Conventional intubation instruments also do not provide real-time documentation of the intubation procedure and the region of interest (e.g., pharynx, larynx, trachea, etc.). Real-time documentation may be necessary for quality assurance/improvement and educational purposes. For example, video data may be useful in identifying unsafe intubation steps and accident precursors and/or evaluating performance of the medical practitioner.

Conventional intubation instruments, such as intubation endoscopes, often have multiple control interfaces (e.g., buttons, knobs, joysticks, levers, switches) for controlling different functions/features of the instrument. However, with multiple control interfaces, a user may engage the wrong control interface (e.g., press the wrong button) because they are looking at a screen displaying the region of interest rather than at the control interfaces on the instrument. The wrong button press would invoke a function or move which would then have to be undone, thereby increasing the overall time for intubating a patient. Further, the control interfaces themselves do not provide an intuitive way for a user to determine the status of a function/feature associated with a particular control interface. For example, even if a user looked down at the intubation instrument to find the desired control interface to manipulate, the user may still have to refocus on the screen or another component of the intubation system in order to ascertain the current status or configuration of the function/feature before engaging the control interface. As a result, conventional instruments do not facilitate correct and expeditious intubation.

Thus, there exists a need in the art for an improved intubation instrument and improved control interface(s) for an intubation instrument.

SUMMARY

The needs set forth herein as well as further and other needs and advantages are addressed by the present embodiments, which illustrate solutions and advantages described below.

It is an object of the present teachings to remedy the above drawbacks and issues associated with conventional intubation instruments.

It is another object of the present teachings to provide an intubation instrument that may be operated in an ergonomic and reliable fashion.

It is a further object to present an intubation instrument having a control interface that provides intuitive ways for a user to determine the status or condition of a function or feature of the instrument.

It is yet another object of the present teachings to provide an intubation instrument having minimal control interfaces (e.g., buttons, knobs, joysticks, levers, switches) for controlling the functions and features of the instrument.

These and other objects of the present teachings are achieved by providing an intubation instrument comprising a proximal end and a distal end, a handle positioned at the proximal end, an imaging system extending between the distal end and the proximal end, the imaging system having an image sensor configured to generate image data, and a control interface disposed on the handle for controlling at least one function of the instrument, the control interface being configured to alternately emit light in different colors, each color indicating at least one state, status or condition of the instrument. The control interface may be a button, such as a command button or a push button. In some embodiments, the control interface may be a multi-functional button, wherein different types of engagements of the control interface commence different functions of the instrument.

The control interface emits a first color to indicate a first state, status or condition of the instrument. A second color is emitted by the control interface to indicate when the instrument is in a second state, status or condition. The first color may, for example, indicate that at least one function of the intubation instrument is enabled and/or available to be initiated by the user. The second color may, for example, indicate that the at least one function of the intubation instrument has been initiated, activated, is operating and/or is currently running. In some embodiments, the first color is blue and the second color is green. However, a person having ordinary skill in the art would understand that the first color and the second color may comprise different colors. For example, the first color may be green and the second color may be yellow.

The intubation instrument may further include a processor or circuitry which processes the image data from the image sensor. In some embodiments, the control interface emits a first color to indicate that the processor is configured or enabled to capture/record at least one image transmitted from the image sensor. That is, when a user sees the first color being emitting by the control interface, it is readily understood by the user that a command signal can be sent to the processor from the control interface in order to capture at least one image by engaging the control interface (e.g., pressing the button). In the case where the control interface is a button, if the user taps once or presses/depresses momentarily the button, a command signal is sent to the processor to capture or record a single image. A tap or momentary press on the button may comprise pushing and holding the button down for a period of time equal to or less than 1 second. During the single image capture (which may include saving the single image into storage), the button emits the second color. Once the single image capture (which may include saving the single image into storage) is completed, the button returns to emitting the first color. Alternatively, if the user presses the button and holds the button down in a depressed state for more than 1 second (e.g., 2 seconds), a command signal is sent to the processor to begin capturing or recording a series of images into storage, wherein the series of images forms a video. The video recording can then be terminated by pressing the button again. Throughout the video recording operation, the button continuously flashes with the second color. The button will revert to emitting the first color when the video recording operation ends, thereby indicating that the processor is configured or enabled to perform a subsequent capture or recording operation.

The intubation instrument may comprise a display monitor in communication with the processor and configured to display at least one of the image data generated by the image sensor, information about the state, status, or condition of the intubation instrument, or other information about the intubation procedure. In some embodiments, the display monitor may be coupled to a part of the intubation instrument, such as the handle. The coupling of the monitor to the intubation instrument may be permanent or conversely, the monitor may be releasably coupled to (i.e., detachable from) the intubation instrument. In other embodiments, the monitor is connected to the intubation instrument via a communications cable, such as USB, fiber optic, Ethernet, or the like. In yet other embodiments, the intubation instrument may comprise a transceiver for wirelessly communicating data between the monitor and the processor.

The intubation instrument may also include a memory storage unit in communication with the processor, wherein the memory storage unit saves single images and/or videos (series of images) captured by the processor. Alternatively, the memory storage unit may be disposed within the monitor. The memory storage unit comprises an internal storage unit. Examples of an internal storage unit include, but are not limited to, an integrated memory card, flash memory, memory cartridge, internal hard drive, and solid state drive. Alternatively, the memory storage unit may be an external storage unit connected via a communications cable (e.g., USB, fiber optic, Ethernet, cable) or connected wirelessly to the processor. Examples of an external storage unit include, but are not limited to, an external hard drive, a solid state drive, flash memory, a computer, and a database server.

In some embodiments, the intubation instrument is a laryngoscope. In other embodiments, the intubation instrument is an intubation endoscope, which can be configured to be combined with a laryngoscope.

The control interface may be configured to control functions other than capturing/recoding image(s). For example, the intubation instrument may comprise a suction assembly for removing debris, such as blood, vomit, or the like, from the patient's airway, and the control interface may be used to turn on/off and/or adjust the suction level of the suction assembly. The suction assembly may include a suction tube with an opening disposed at or proximate to the distal end of the intubation instrument. The proximal end of the suction tube is connected to a suction/vacuum source. The control interface may emit a first color to indicate that suction is turned off, while the control interface may emit a second color to indicate that suction has been turned on by the user. In another example, the intubation instrument includes an illumination system to direct light out of the distal end of the intubation instrument and provide illumination of a patient's airway, wherein the control interface may be used to turn on/off the illumination system and/or adjust the light intensity of the illumination system. The first color emitted by the control interface, for example, may indicate that the illumination system is off. If the user presses the control interface (e.g., button) once, the illumination system is powered on to a low illumination setting and the control interface emits a second color. If the user subsequently presses the control interface again, the intensity of the illumination is increased to a high(er) setting and the control interface emits a third color. Although the above functions have been described, a person having ordinary skill in the art would understand the emission of different colors by the control interface may serve to indicate the state, status or condition of other known functions/operations of an intubation instrument (e.g., laryngoscope, intubation endoscope).

The present teachings also provide an intubation instrument comprising a proximal end and a distal end, a handle positioned at the proximal end of the instrument, an imaging system extending between the distal end and the proximal end, the imaging system having an image sensor configured to generate image data, and a control interface disposed on the handle for controlling at least one function of the instrument, the control interface being configured to alternately emit light in at least three different colors, such that three or more different states, statuses or conditions of a function (e.g., image capturing/recording, suction, illumination, etc.) of the instrument can be indicated. Thus, the user can intuitively recognize from the light color of the control interface what the state, status or condition of the instrument is in.

The present teachings also provide an intubation instrument comprising a proximal end and a distal end, a handle positioned at the proximal end of the instrument, an imaging system extending between the distal end and the proximal end, the imaging system having an image sensor configured to generate image data, and a control interface disposed on the handle for controlling at least one function of the instrument, the control interface being configured to provide different types of emission of light, wherein each type of emission indicating at least one state, status or condition of the instrument. For example, the control interface may emit no light to represent a first state of a function (e.g., image capturing/recording, suction, illumination, etc.) of the instrument. Control interface may emit a steady light to represent a second state and a constant flashing light to represent a third state. In addition, the speed of the flashing light may further indicate different states of the function of the instrument. A first speed of the flashing light may represent the third state, whereas if the control interface emits a flashing light at a second, faster speed, a fourth state is indicated.

Other features and aspects of the invention will become apparent from the following detailed description, taken in conjunction with the accompanying drawings, which illustrated by way of example the features in accordance with embodiments of the invention. The summary is not intended to limit the scope of the invention, which is defined solely by the claims attached thereto.

BRIEF DESCRIPTION OF THE DRAWINGS

It should be understood that through the drawings, corresponding reference numerals indicate like or corresponding parts and features.

DETAILED DESCRIPTION

The present teachings are described more fully hereinafter with reference to the accompanying drawings, in which the present embodiments are shown. The following description illustrates the present teachings by way of example, not by way of limitation of the principles of the present teachings.

The present teachings have been described in language more or less specific as to structural features. It is to be understood, however, that the present teachings are not limited to the specific features shown and described, since the devices herein disclosed comprise preferred forms of putting the present teachings into effect.

Figure 1:
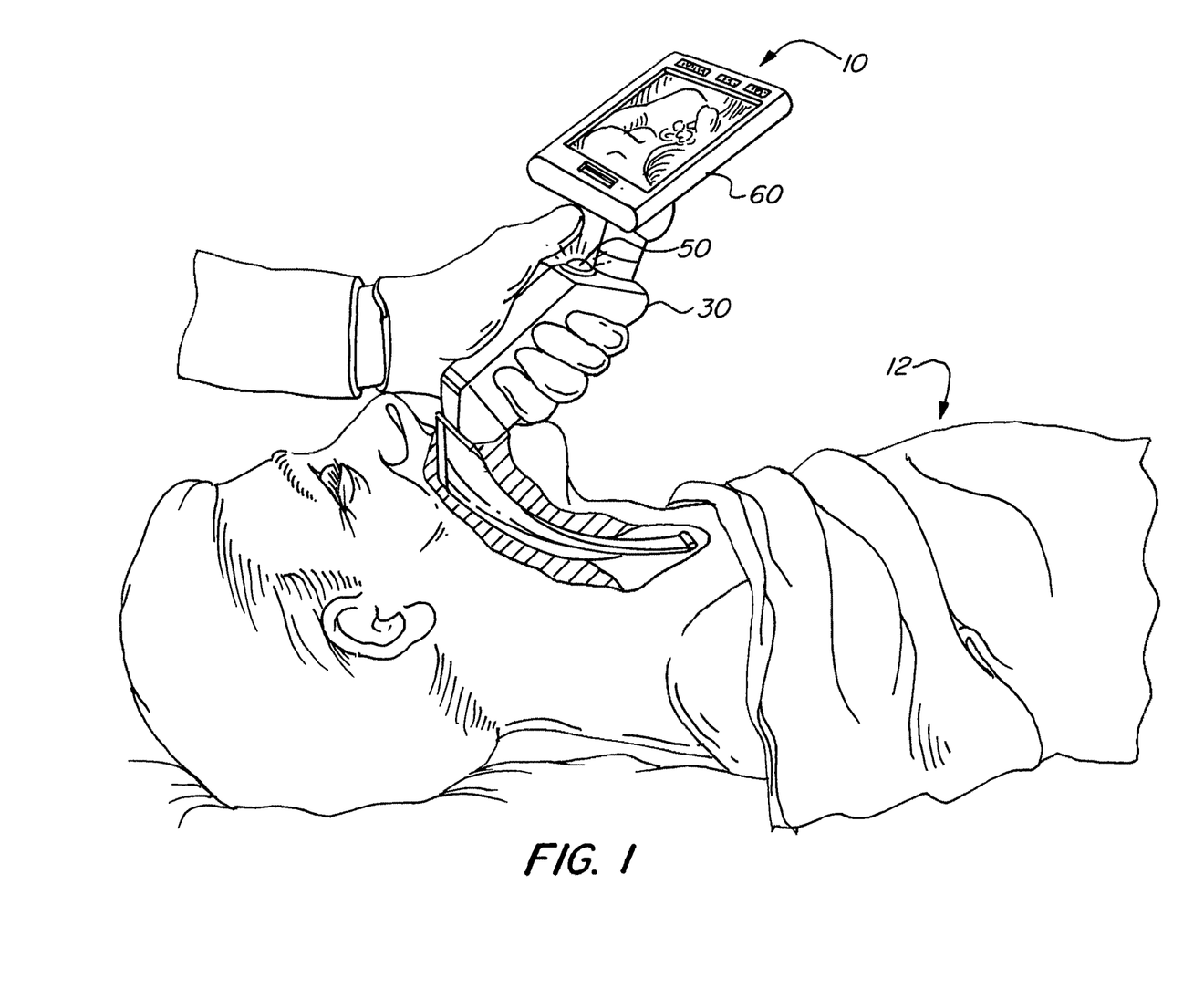
FIG. 1 is a perspective view of an intubation instrument in accordance with the present teachings, wherein the intubation instrument is being used in a patient.
Figure 4:
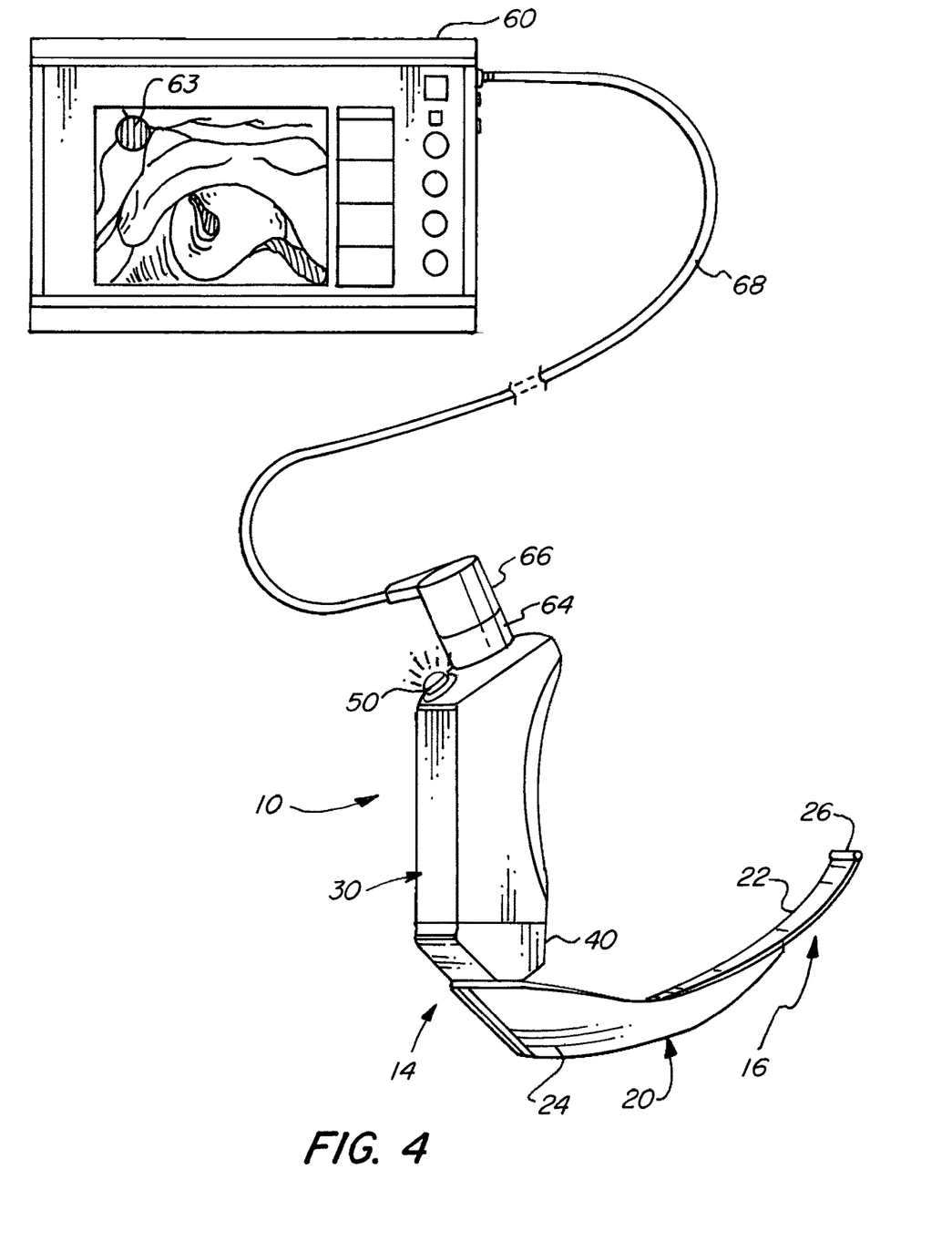
FIG. 4 is a perspective view of the intubation instrument of FIG. 1 with a monitor connected to the instrument via a communications cable.
Figure 5:
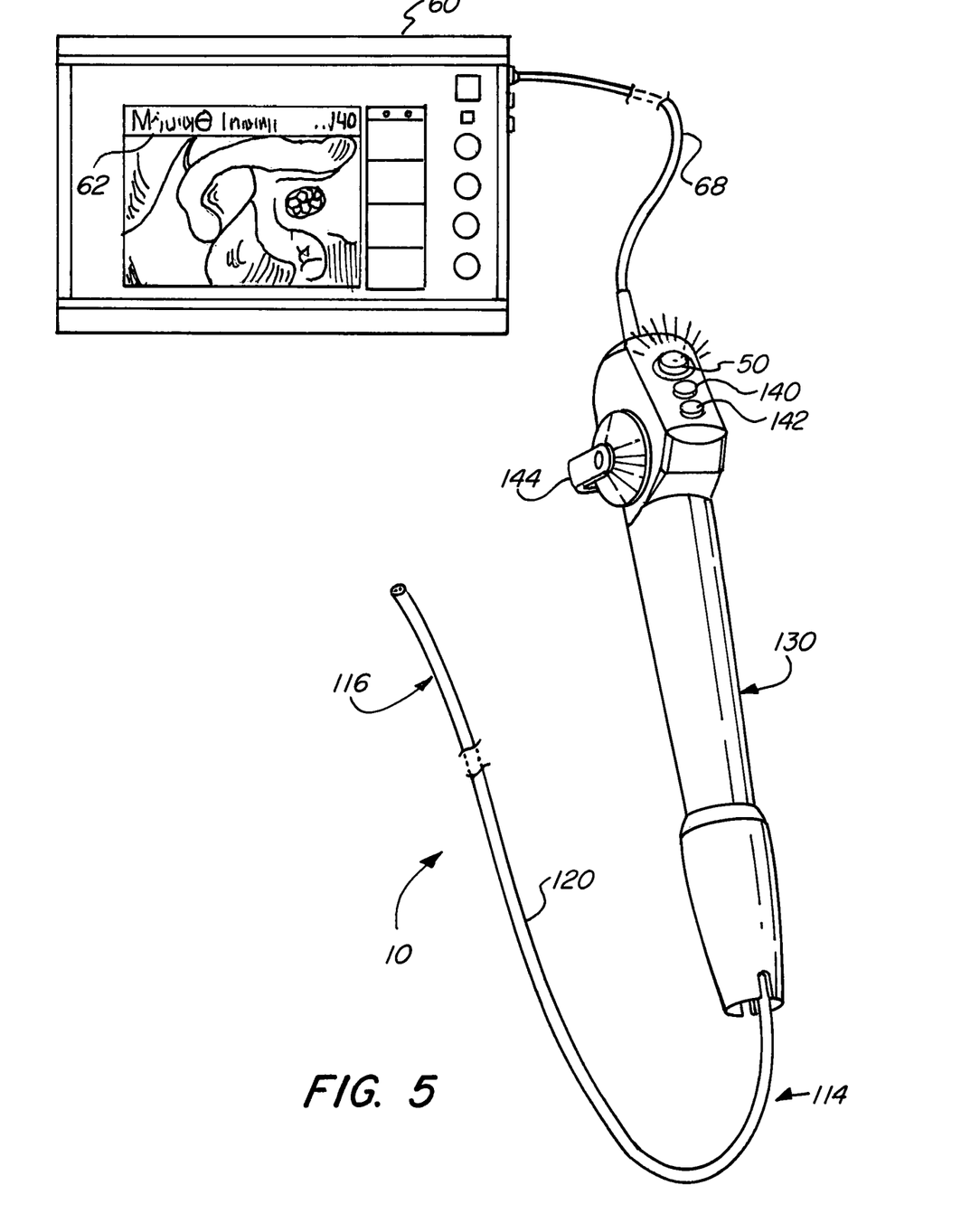
FIG. 5 is a perspective view of another embodiment of the intubation instrument in accordance with the present teachings.

Referring to FIG. 1, a perspective view of an intubation instrument 10 is shown being used in a patient 12. The intubation instrument 10 has been inserted into the patient's airway through the mouth. The intubation instrument 10 extends just outside of the patient's trachea, thereby providing views of the patient's trachea. The intubation instrument, as shown in FIGS. 1-4, is a laryngoscope. In other embodiments, the intubation instrument is an intubation endoscope as shown in FIG. 5.

Figure 2:
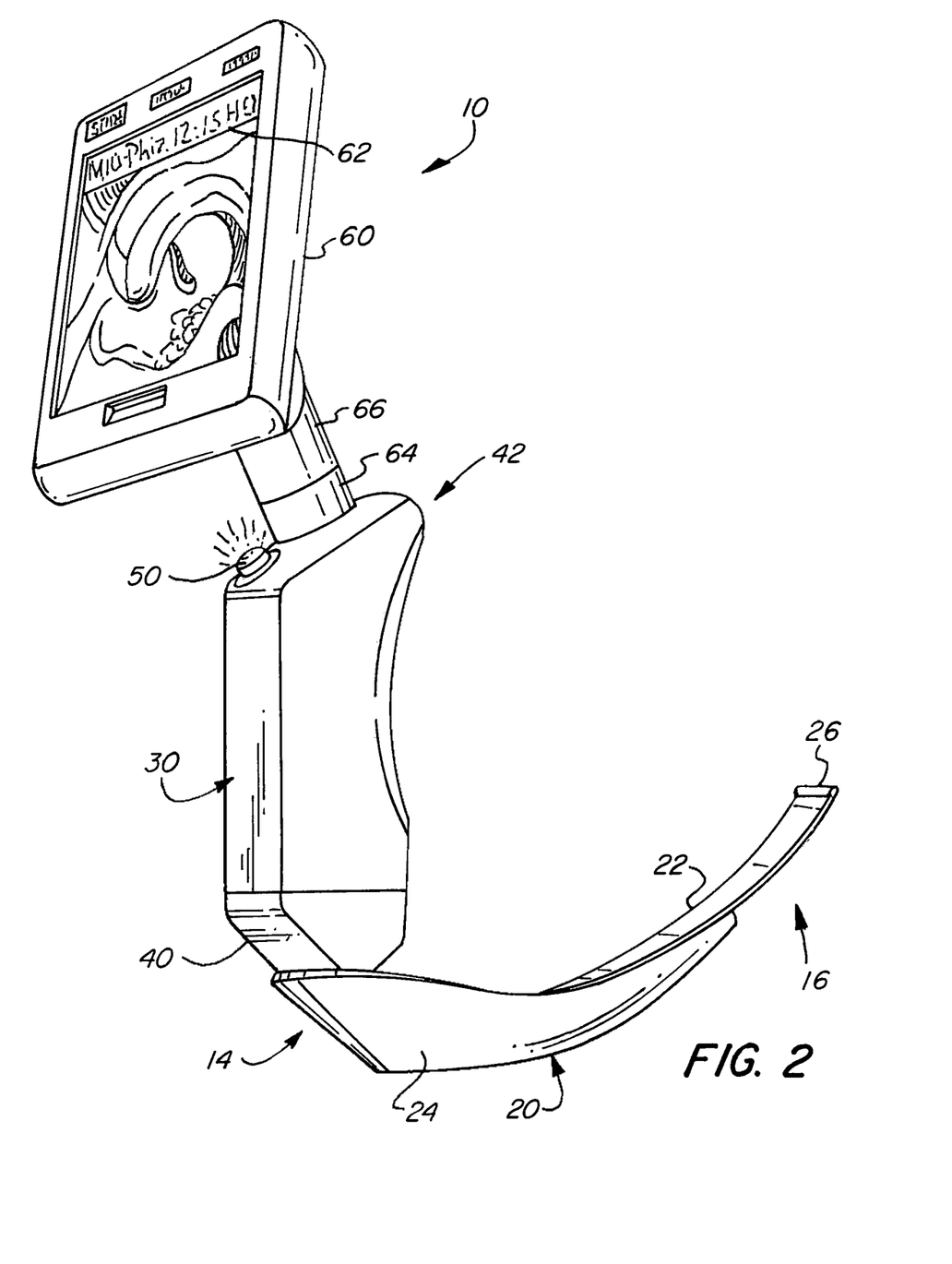
FIG. 2 is a perspective view of the intubation instrument of FIG. 1.
Figure 3:
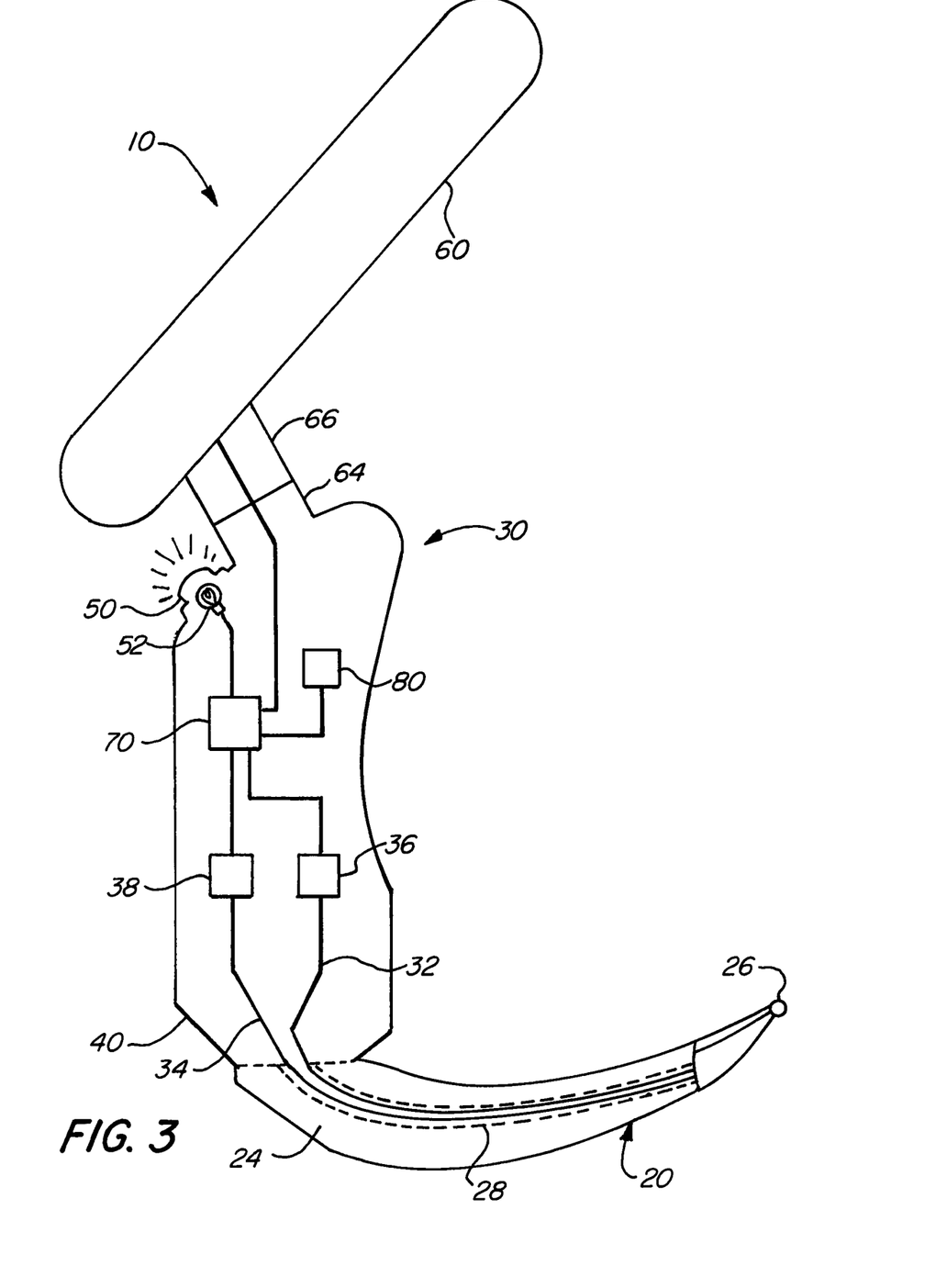
FIG. 3 is a side view of the intubation instrument of FIG. 1 showing schematically the internal components of the instrument.

FIGS. 1-3 show the intubation instrument 10 has a spatula 20 extending from a proximal end 14 to a distal end 16 of the instrument. A handle 30 is disposed at the proximal end 14 and connected to the spatula 20 by means of a coupling 40. The handle 30 may include one or more finger grooves to provide an ergonomic design for easy gripping of the instrument. The spatula 20 comprises a spatula blade 22 and a lateral wall 24, which projects substantially vertically relative to the blade 22. At its distal end, the spatula blade 22 comprises a bead 26. The spatula further includes a tube or channel 28, which accommodates both an illumination system 32 and imaging system 34. At the distal end of the channel 28, the illumination system 32 includes a light exit opening and the imaging system 34 includes an image entry opening.

The illumination system may comprise one or more waveguide strings (e.g., optical fibers, lenses) which transmit illumination from an illumination source 36 towards the distal end 16 and out of the light exit opening in order to illuminate the patient's airway. The illumination source 36 may be disposed within the handle 30, as shown in FIG. 3, or alternatively, in the spatula 20, for example, proximate to the distal end of the spatula 20.

The imaging assembly 34 may comprise an image guide (e.g., optical fiber, lenses) extending from the image entry opening at the distal portion of the spatula 20 to an image sensor 38, which generates image data corresponding to a view of the region of interest in front of the distal end of the intubation instrument. In some embodiments, the image sensor 38 is disposed within the handle 30, as shown in FIG. 3. Alternatively, the image sensor 38 may be disposed within the spatula 20, for example, at or proximate to the distal end of the spatula 20. In such an embodiment, the image sensor generates the image data as an electrical signal that is transmitted from the distal end to the proximal end of the instrument for display and/or storage. The image sensor 38 may comprise a charge-coupled device (CCD) sensor, complementary metal-oxide semiconductor (CMOS) sensor, or the like.

The intubation instrument 10 also comprises at least one control interface 50 for controlling at least one function of the intubation instrument 10. The control interface 50 is configured to accept instructions/commands from the user to the intubation instrument. As shown in FIGS. 1-3, the control interface is positioned at or proximate to a proximal end 42 of the handle 30, which is opposite the distal end of the handle where the coupling 40 is disposed. The control interface 50 is positioned for easy engagement by a user's finger (e.g., thumb). The control interface 50 may be a button, knob, joystick, lever, switch, or other mechanical device through which a user input can be provided to the instrument for controlling a function or operation of the instrument. In a preferred embodiment, the control interface 50 is a push button.

The control interface 50 is configured to alternately emit light in different colors, wherein each color indicates a different state, status and/or condition of the intubation instrument, and more specifically, a state, status and/or condition of a function of the intubation instrument. For example, emission of light in a first color by the control interface 50 signifies that the intubation instrument (function thereof) is in a first state, while emission of light in a second color may signify that the intubation instrument (function thereof) is in a second state. Accordingly, the color of light emitted by the control interface 50 changes when or as long as the control interface is engaged (e.g., pressed) by a user, such engagement initiating a function of the intubation instrument. In one embodiment, the first color is blue and the second color is green. In another embodiment, the first color is blue and the second color is red. Still, in another embodiment, the first color may be green and the second color is red. It is noted that the above colors are exemplary and the control interface may be configured to emit other colors (wavelengths) within the visible spectrum to indicate the first and second states of the intubation instrument.

The control interface 50 in some instances may also be configured to emit light in more than two colors (e.g., 3, 4, 5, etc.) such that it can indicate additional states, statuses, and/or conditions of the intubation instrument. The different colored lights that the control interface emits enable a user to readily or intuitively determine what state the intubation instrument is currently in, especially without having to refer to a graphical display on a monitor.

The control interface includes a light source 52 which is adapted to emit different-colored light, as shown in FIG. 3. The light source 52 is disposed within the control interface 50 (e.g., button) or within the handle 30 proximate to and/or aligned with the control interface 50. In some embodiments, the light source comprises a plurality of dedicated-color light emitting diodes (LEDs), wherein the number of LEDs matches the number of colors which the control interface 50 is configured to emit. That is, each LED corresponds to one particular color that the control interface is configured to emit. In other embodiments, the light source 52 may comprise a red LED, green LED, and blue LED. By independently adjusting each of the three, the RGB LEDs are capable of producing a wide color gamut or multiple hues of light. The control interface 50, itself, may be composed—partially or entirely—of transparent, semi-transparent, or translucent material to allow the light from the light source 52 to pass through.

The intubation instrument 10 comprises a display monitor 60 configured to display the image data generated by the imaging system 34, and in particular, the image sensor 38. Prior to the image data being transmitted to the monitor 60, the image data or image signal may be processed by a processor or processing unit 70. In some embodiments, the processor 70 is disposed within the intubation instrument 10, such as in the handle 30. However, other embodiments provide for the processor 70 to be disposed within the monitor 60. Different types of processing operations (e.g., image sharpening, image smoothing, image compression, filtering, conversion, manipulation, overlaying, etc.) may be performed on the image data before it is displayed on the monitor 60. Accordingly, the monitor 60 provides the user with visualization of a region of interest (e.g., patient's pharynx, larynx, trachea, etc.) to facilitate the insertion of the intubation instrument 10 into the patient 12. The monitor 60 is also configured to display information about the current state, status, and/or condition of the intubation instrument and functions thereof. For example, a section 62 of the monitor's graphical user interface may show status information. As shown in FIG. 2, section 62 appears as a top bar containing text and/or icons which indicates and/or provides data relating to the current status of the intubation instrument. In other embodiments, the section 62 may be displayed in other parts of the monitor's graphical user interface, such as the left side, right side, bottom, or corners. The status information shown, in particular, includes at least information about the status of the function which is controllable by the control interface 50, and more specifically shows status information which corresponds to the status indication provided by the color of the light emitted by the control interface 50. In some embodiments, the section 62 displays a background color which matches or at least corresponds to the color of the light emitted by control interface 50. As one example, if the control interface 50 is emitting a first color (e.g., blue), the monitor 60 displays section 62 also with the first color (e.g., blue). When the status of the intubation instrument 10 changes, for example due to the user engaging the control interface 50, both the control interface 50 and the monitor 60 are updated to show a second color (e.g., green).

As shown in FIGS. 1-3, the monitor 60 may be releasably coupled to a part of the intubation instrument, for example, the proximal end 42 of the handle 30. The monitor 60 may therefore be decoupled from the intubation instrument for purposes of cleaning the intubation instrument or replacing the intubation instrument with another. To achieve the releasable/detachable coupling, the intubation instrument 10 includes a female or male connector 64 which mates respectively with a male or female connector 66 on the monitor 60. When connection between the connectors 64, 66 is made, communication between the intubation instrument 10 and the monitor 60 is established, thereby enabling the image data from the image sensor 38 and/or processed image data from the processor 70 to be transmitted to the monitor for display. The monitor 60 also has a swivel mechanism and tilt mechanism with which to adjust the position and orientation of the monitor according to user preference. With this particular configuration, the user can hold both the intubation instrument and the monitor together in one hand while have the other hand free to perform other actions. In other embodiments, such as shown in FIG. 4, the monitor 60 is releasably connected to the intubation instrument 10 via a communications cable 68. The communications cable can be disconnected from both the monitor 60 and the intubation instrument 10. The communications cable, for example, may comprise USB, fiber optic, Ethernet, or the like. With this configuration, the user has even more flexibility in positioning and orienting the monitor 60 according to user preference.

Referring back to FIG. 3, the processor or processing unit 70 is connected to the illumination source 36 and the image sensor 38 to control and/or receive data from these components. The processor 70 is also connected to the control interface 50 to receive control/command signals when the control interface is engaged by the user. For example, the control interface 50 may be configured to send control signals to the processor 70 to initiate and/or terminate image capturing-recording operations. However, other functions may be controllable by the control interface 50, such as adjusting suction level of a suction assembly disposed in the intubation instrument or adjusting the intensity level of the illumination source 36. In some embodiments, the control interface 50 is a multifunctional control interface 50 (e.g., multifunction push button). The multi-functionality of the control interface enables different command/control signals—for adjusting functions of the intubation instrument—to be transmitted to the processor by providing different user inputs to the control interface, and more specifically, by engaging the control interface in a plurality of different ways. The intubation instrument 10, and in particular, the processor 70, is configured to discriminate between short and long engagement/activation of the multifunctional button 50. A short engagement may comprise tapping the button 50 or a short press on the button 50 for a period of time, for example, equal to or less than 1 second. A long engagement may comprise a long press on the button 50 for more than 1 second, or for 2 or more seconds. In some embodiments, the button 50 is adapted to send different control signals (and thus adjust functions of the intubation instrument) based on the number of short presses. For example, one short press may control the instrument to perform one function, two successive short presses may control the instrument to perform another function, and further three successive short presses may control the instrument to perform yet another function.

The intubation instrument 10 may be configured such that the processor 70 is connected to the light source 52 of the control interface 50 and controls the color of the light emitted by the light source 52. When a user engages (e.g., presses down) the control interface 50 to initiate/activate or adjust a function of the intubation instrument, a command/control signal is sent to the processor 70, which, in response, sends a color signal to the light source 52 indicating what color light to provide. Similarly, the processor 70 sends the same color signal to the monitor 60 so that the section 62 of the graphical user interface displays the same or corresponding color as the control interface 50. In other embodiments, the control interface 50 may be configured so that the command/control signals generated upon user engagement is sent directly to the light source 52, wherein the light source 52 adjusts the color of the light emitted based on the command/control signal. The light source 52 simultaneously transmits a color signal to the processor 70 so that the section 62 displays the same or corresponding color as the control interface 50. It is noted that other configurations of the control interface 50, light source 52, processor 70 and monitor 60 which satisfy the requirements described herein may be suitable for implementing the intubation instrument.

In an exemplary embodiment of the intubation instrument, the control interface 50 controls the image capturing/recording function of the intubation instrument 10 and alternately emits light in different colors to indicate different states, statuses, conditions of the image capturing/recording function. The control interface as a multifunctional button can activate a single image capture or video recording (i.e., capturing a series of images). The single image capture and video recording includes the process of saving the single image or video into storage. After the intubation instrument 10 and/or monitor 60 is powered on, the multifunctional button emits light, via the light source 52, in a first color (e.g., blue). The monitor 60 displays section 62 of the graphical user interface also with the first color. The first color indicates that the image capturing/recording function is enabled. As such, a user seeing the first color emitted by the control interface 50 and/or seeing the first color displayed in section 62 will readily understand that the image capturing/recording function is available for initiation/activation. When a user, for example, applies a short engagement (e.g., short press on the button), a command signal is sent to the processor 70 to capture a single image from the image data provided by the image sensor and to store the single image. At the same time or immediately thereafter, the light source 52 is configured to emit light in a second color (e.g., green). The control interface 50 therefore lights up briefly with the second color during the single image capture (and storage) and then switches back to the first color upon completion of the single image capture (and storage). In some embodiments, during the single image capture process, the monitor also displays section 62 of the graphical user interface with the second color, as well as displays other status information including the remaining storage capacity of a memory storage unit and/or the file size of the single image. After the single image capture (and storage) ends, the section 62 reverts back to the first color. If instead of a short press, the user applies a long engagement (e.g., long press on the button), a command signal is sent to the processor 70 to record video, i.e., capture and store a series of images, wherein the series of images forms a video. At the same time or immediately thereafter, the light source 52 is configured to emit a flashing light in the second color (e.g., green) during the video recording process. The monitor 60 simultaneously displays section 62 of the graphical user interface with the second color as well as displays other status information. The other status information provided by the monitor may include the remaining storage capacity of the memory storage unit in minutes, the number of directory, file location, length of time of the recording as well as a symbol showing that video recording is running. In some embodiments, the monitor displays section 62 with the second color for a few seconds (e.g., 1-3 second), and thereafter, replaces section 62 with a video recording symbol 63 in the form of a solid red circle, as shown in FIG. 4. To terminate or end the video recording process, the user merely presses the multifunctional button once (e.g., short engagement), which commands the processor 70 to cease recording operations. The multifunctional button further switches back to emitting a constant light in the first color when the video recording ends.

The intubation instrument may further comprise a memory storage unit 80 connected to the processor 70. The memory storage unit is configured to save the single image and/or video captured by the processor. The memory storage unit may comprise an internal storage unit, such as an integrated memory card, flash memory, memory cartridge, internal hard drive, or solid state drive. As shown in FIG. 3, the memory storage unit 80 may be disposed within the handle 30 of the intubation instrument 10. In other embodiments, the memory storage unit may be disposed within the monitor 60. In yet other embodiments, the memory storage unit 80 is an external storage unit communicating with the processor, by way of a communications cable (e.g., USB, fiber optic, Ethernet, cable), or wirelessly.

Referring to FIG. 5, the intubation instrument 10 is an intubation endoscope. The endoscope comprises a shaft 120, which has a proximal end 114 and a distal end 116. The shaft comprises a central longitudinal axis and may be moved between a linearly straightened state and a state laterally deflected to a side. In some embodiments, a proximal section of the shaft 120 is rigid (straight or curved) and a distal section of the shaft is deflectable. A handle 130 is connected to the proximal end 114 of the shaft 120. The handle may include a gripping surface and/or grooves to provide an ergonomic design for easy gripping of the instrument.

The intubation endoscope shown in FIG. 5 has many of the same internal components and mechanisms described above with respect to FIGS. 1-4. For example, the shaft includes one or more tubes and channels extending from the proximal end 114 to the distal end 116, wherein the channel(s) accommodate both an illumination system 32 and an imaging system 34. At the distal end of the shaft 120, a light exit opening and an image entry opening is provided for the illumination system and the imaging system, respectively. The illumination system may comprise one or more waveguide strings (e.g., optical fibers, lenses) which transmit illumination from an illumination source towards the distal end and out of the light exit opening in order to illuminate the patient's airway. The illumination source may be disposed within the handle 130. Alternatively, the illumination source may be disposed at or proximate to the distal end 116 of the shaft 120. The imaging assembly may comprise an image guide (e.g., optical fiber, lenses) extending from the image entry opening at the distal end 116 of the shaft to an image sensor, which generates image data corresponding to a view of the region of interest in front of the distal end of the intubation endoscope. The image sensor may be disposed within the handle 130. As an alternative, the image sensor may be disposed at or proximate to the distal end 116 of the shaft 120. The intubation endoscope may also include a processor 70 disposed in the intubation endoscope 10 or within a monitor 60, as well as a memory storage unit 80 disposed in the intubation endoscope 10 or within the monitor 60. The processor and the memory storage unit have the same characteristics described above with respect to FIGS. 1-4. The monitor 60 is connected to the intubation endoscope via a communications cable 68 (USB, fiber optic, Ethernet, or the like). The monitor is configured to display the image data generated by the image sensor.

Like the laryngoscope in FIGS. 1-4, the intubation endoscope of FIG. 5 comprises at least one control interface, and for example, a plurality of control interfaces 50, 140, 142, 144, as shown in FIG. 5. The control interfaces 140, 142 may be configured to adjust suction and illumination settings. The control interface 50 may be configured to control an image capturing-recording function. The control interface 144, in the form of a lever, may be configured to deflect the shaft. One or more of the control interfaces are configured to alternately emit light in different colors, wherein each color indicates a different state, status and/or condition of the intubation instrument, and more specifically, a state, status and/or condition of a corresponding function of the intubation instrument. For example, control interface 50 includes a light source which is adapted to emit different-colored light. The characteristics of the control interface 50, light source 52, processor 70 and monitor 60 described with respect to the laryngoscope in FIGS. 1-4 are applicable to the intubation endoscope in FIG. 5.

It should be understood to a person of ordinary skill in the art that different configurations of the intubation instrument are possible. For example, in some embodiments, the intubation instrument is a laryngoscope with a monitor detachably coupled to a portion (e.g., handle) of the laryngoscope. In other embodiments, the intubation instrument is a laryngoscope connected to a monitor via a communications cable. In some embodiments, the intubation instrument is a video endoscope with a monitor detachably coupled to a portion (e.g., handle) of the endoscope. In yet other embodiments, the intubation instrument is a video endoscope connected to a monitor via a communications cable.

While the present teachings have been described above in terms of specific embodiments, it is to be understood that they are not limited to those disclosed embodiments. Many modifications and other embodiments will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

What is claimed is:

1. A medical intubation instrument comprising:
a proximal end and a distal end;
a handle positioned at the proximal end;
a control interface disposed on or proximate to the handle, the control interface being configured to receive user input and to control at least one function of the instrument based on said user input;
the control interface having a light source disposed within the control interface and configured to illuminate at least a portion of the control interface, the light source configured to alternately emit light in different colors, each color indicating a status, state or condition of the function of the instrument;
wherein the at least one function is an image capture-recording function of the instrument; and
wherein the light source is configured to alternately emit light in different colors to indicate when the instrument is ready for image capture or video recording, when a single image is captured, and when a video is being recorded.

2. The medical intubation instrument of claim 1, wherein the light source is configured to alternate between emitting light in a first color and light in a second color in response to the control interface receiving said user input; and
wherein the control interface, when illuminated in the first color, is configured to indicate a first status, state or condition of the function, and the control interface, illuminated in the second color, is configured to indicate a second status, state or condition of the function.

3. The medical intubation instrument of claim 1, further comprising:
an imaging system extending from the distal end to the proximal end of the instrument, the imaging system having an image sensor configured to generate image data; and
a display monitor displaying at least one of the image data, the state, status or condition of the at least one function of the instrument, or intubation procedure information;
wherein the monitor is releasably coupled to a part of the instrument having the control interface.

4. The medical intubation instrument of claim 3, wherein the monitor is coupled directly to the part of the instrument having the control interface via a first mating connector disposed on the monitor and a second mating connector disposed on the part of the instrument having the control interface.

5. The medical intubation instrument of claim 3, wherein the monitor is coupled to the part of the instrument having the control interface via a communications cable.

6. The medical intubation instrument of claim 3, wherein the monitor is configured to display a graphical interface having at least one status indicator, and wherein the status indicator is configured to display in a color which corresponds to the color of the light simultaneously emitted by the light source within the control interface.

7. The medical intubation instrument of claim 6, wherein the graphical interface of the monitor has multiple status indicators, and wherein the multiple status indicators are configured to display in colors corresponding to the colors of the light emitted by the light source within the control interface.

8. The medical intubation instrument of claim 1, wherein the control interface is a push button, and wherein the color of the light configured to be emitted by the light source changes when the button is pressed.

9. The medical intubation instrument of claim 8, wherein the button is a multifunctional button; and
wherein the instrument further comprises a processor connected to the button and configured to receive command signals from the button to initiate the at least one function of the instrument, the processor being configured to discriminate between a short press and a long press on the button, the short press adjusting the function from a first status, state or condition to a second status, state or condition, and the long press adjusting the function from a first status, state or condition to a third status, state or condition.

10. The medical intubation instrument of claim 9, wherein when the function switches from the first status, state or condition to the second status, state or condition, the light source is adjusted from emitting light in a first color to emitting light in a second color; and
   wherein when the function switches from the first status, state or condition to the third status, state or condition, the light source is adjusted from emitting light in a first color to flashing light in the second color.

11. The medical intubation instrument of claim 9, wherein when the function switches from the first status, state or condition to the second status, state or condition, the light source is adjusted from emitting light in a first color to emitting light in a second color; and
   wherein when the function switches from the first status, state or condition to the third status, state or condition, the light source is adjusted from emitting light in a first color to emitting light in a third color.

12. The medical intubation instrument of claim 1, wherein:
   when neither a single image is captured nor a video is being recorded, the control interface is configured to emit light in a first color;
   during a period when a single image is being captured, the control interface is configured to emit light in a second color; and
   during a period when a video is being recorded, the control interface is configured to emit one of a flashing light in the second color or a steady light in a third color.

13. The medical intubation instrument of claim 1, wherein the light source comprises a plurality of light emitting diodes.

14. The medical intubation instrument of claim 1, wherein the instrument is a laryngoscope.

15. The medical intubation instrument of claim 1, wherein the instrument is an intubation endoscope.

16. A medical intubation instrument comprising:
   a proximal end and a distal end;
   a handle positioned at the proximal end;
   a control interface disposed on or proximate to the handle, the control interface being configured to receive user input and to control at least one function of the instrument based on said user input;
   the control interface having a light source configured to illuminate at least a portion of the control interface from within, the light source being configured to emit light in one of a plurality of colors, wherein each of the plurality of colors is configured to indicate a status, state or condition of the function of the instrument;
   a processor connected to the control interface, the control interface configured to transmit a command signal to the processor upon receiving said user input, the processor configured to adjust the status, state or condition of the function based on the command signal;
   an imaging system configured to generate image data corresponding to a view of a region of interest in front of the distal end and configured to transmit the image data to the processor for processing, and
   a monitor in communication with the processor and configured to display the processed image data and a graphical interface, wherein a section of the graphical interface includes information about the state, status or condition of the instrument;
   wherein the section of the graphical interface is displayed in a color corresponding to the color of light simultaneously emitted by the light source, and
   wherein, in response to receiving the command signal, the processor is configured to transmit a color signal to the light source to switch from a first color to a second color.

17. The medical intubation instrument of claim 16, wherein the control interface is a push button, the push button comprising at least one of a transparent, semi-transparent, or translucent material, the material providing for the light emitted by the light source to pass through and out of the button.

18. A medical intubation instrument comprising:
   a proximal end and a distal end;
   a handle positioned at the proximal end;
   a control interface disposed on or proximate to the handle, the control interface being configured to receive user input and to control at least one function of the instrument based on said user input;
   the control interface having a light source disposed within the control interface and configured to illuminate at least a portion of the control interface, the light source configured to alternately emit light in different colors, each color indicating a status, state or condition of the function of the instrument;
   wherein the control interface is a multifunctional push button, and wherein the color of the light configured to be emitted by the light source changes when the button is pressed; and
   wherein the instrument further comprises a processor connected to the button and configured to receive command signals from the button to initiate the at least one function of the instrument, the processor being configured to discriminate between a short press and a long press on the button, the short press adjusting the function from a first status, state or condition to a second status, state or condition, and the long press adjusting the function from a first status, state or condition to a third status, state or condition.

19. The medical intubation instrument of claim 18, wherein when the function switches from the first status, state or condition to the second status, state or condition, the light source is adjusted from emitting light in a first color to emitting light in a second color; and
   wherein when the function switches from the first status, state or condition to the third status, state or condition, the light source is adjusted from emitting light in a first color to flashing light in the second color.

20. The medical intubation instrument of claim 18, wherein when the function switches from the first status, state or condition to the second status, state or condition, the light source is adjusted from emitting light in a first color to emitting light in a second color; and
   wherein when the function switches from the first status, state or condition to the third status, state or condition, the light source is adjusted from emitting light in a first color to emitting light in a third color.

21. A medical intubation instrument comprising:
   a proximal end and a distal end;
   a handle positioned at the proximal end;
   a control interface disposed on or proximate to the handle, the control interface being configured to receive user input and to control at least one function of the instrument based on said user input;
   the control interface having a light source disposed within the control interface and configured to illuminate at least a portion of the control interface, the light source configured to alternately emit light in different colors, each color indicating a status, state or condition of the function of the instrument;

an imaging system extending from the distal end to the proximal end of the instrument, the imaging system having an image sensor configured to generate image data; and a display monitor displaying at least one of the image data, the state, status or condition of the at least one function of the instrument, or intubation procedure information;

wherein the monitor is releasably coupled to a part of the instrument having the control interface;

wherein the monitor is configured to display a graphical interface having at least one status indicator, and wherein the status indicator is configured to display in a color which corresponds to the color of the light simultaneously emitted by the light source within the control interface.

22. The medical intubation instrument of claim 21, wherein the graphical interface of the monitor has multiple status indicators, and wherein the multiple status indicators are configured to display in colors corresponding to the colors of the light emitted by the light source within the control interface.

23. An intubation instrument comprising:
a proximal end and a distal end;
a handle positioned at the proximal end;
an imaging system extending from the distal end to the proximal end of the instrument, the imaging system having an image sensor configured to generate image data;

a control interface disposed on or proximate to the handle, the control interface being configured to receive user input and to control an image capture-recording function of the instrument based on said user input;

a display monitor configured to display at least one of the image data, the state, status or condition of the image capture-recording function, or intubation procedure information; and a processor connected to the control interface, the control interface configured to transmit a command signal to the processor upon receiving said user input, the processor configured to adjust the status, state or condition of the image capture-recording function based on the command signal;

the control interface having a light source disposed within the control interface and configured to illuminate at least a portion of the control interface, the light source being configured to emit light in a first color or a second color;

wherein the control interface emitting light in the first color indicates that processor is ready for image capture or video recording, wherein the control interface emitting light in the second color indicates that a single image is being captured, and wherein the control interface emitting a flashing light in the second color indicates that a video is being recorded.

* * * * *